United States Patent [19]

Sachtler et al.

[11] Patent Number: 5,053,558

[45] Date of Patent: Oct. 1, 1991

[54] PROCESS THE ISOMERIZATION OF CRESOLS

[75] Inventors: J. W. Adriaan Sachtler, Des Plaines; R. Joe Lawson, Palatine, both of Ill.

[73] Assignee: UOP, Des Plaines, Ill.

[21] Appl. No.: 547,705

[22] Filed: . Jul. 3, 1990

Related U.S. Application Data

[60] Continuation-in-part of Ser. No. 394,038, Aug. 14, 1989, Pat. No. 4,939,110, which is a division of Ser. No. 259,086, Oct. 17, 1988, Pat. No. 4,899,012.

[51] Int. Cl.$^5$ ...................... C07C 37/00; C07C 39/07
[52] U.S. Cl. ................................... 568/783; 568/780
[58] Field of Search ............................ 568/783, 780

[56] References Cited

U.S. PATENT DOCUMENTS

| | | | |
|---|---|---|---|
| 4,283,571 | 8/1981 | Keim et al. | 568/783 |
| 4,503,269 | 3/1985 | Engel et al. | 568/783 |
| 4,538,008 | 8/1985 | Firth et al. | 568/783 |
| 4,590,306 | 5/1986 | Korff et al. | 568/783 |
| 4,709,102 | 11/1987 | Gupta | 568/783 |

FOREIGN PATENT DOCUMENTS

| | | | |
|---|---|---|---|
| 432123 | 11/1974 | U.S.S.R. | 568/783 |
| 2012271 | 7/1979 | United Kingdom | 568/783 |

Primary Examiner—Werren B. Lone
Attorney, Agent, or Firm—Thomas K. McBride; John F. Spears, Jr.; Richard E. Conser

[57] ABSTRACT

An improved process is disclosed for the isomerization of a non-equilibrium mixture of cresols to achieve a high yield of one or more cresol isomers using a catalyst comprising a Group VIII metal, a modifier, a pentasil zeolite, and an inorganic oxide binder.

15 Claims, 1 Drawing Sheet

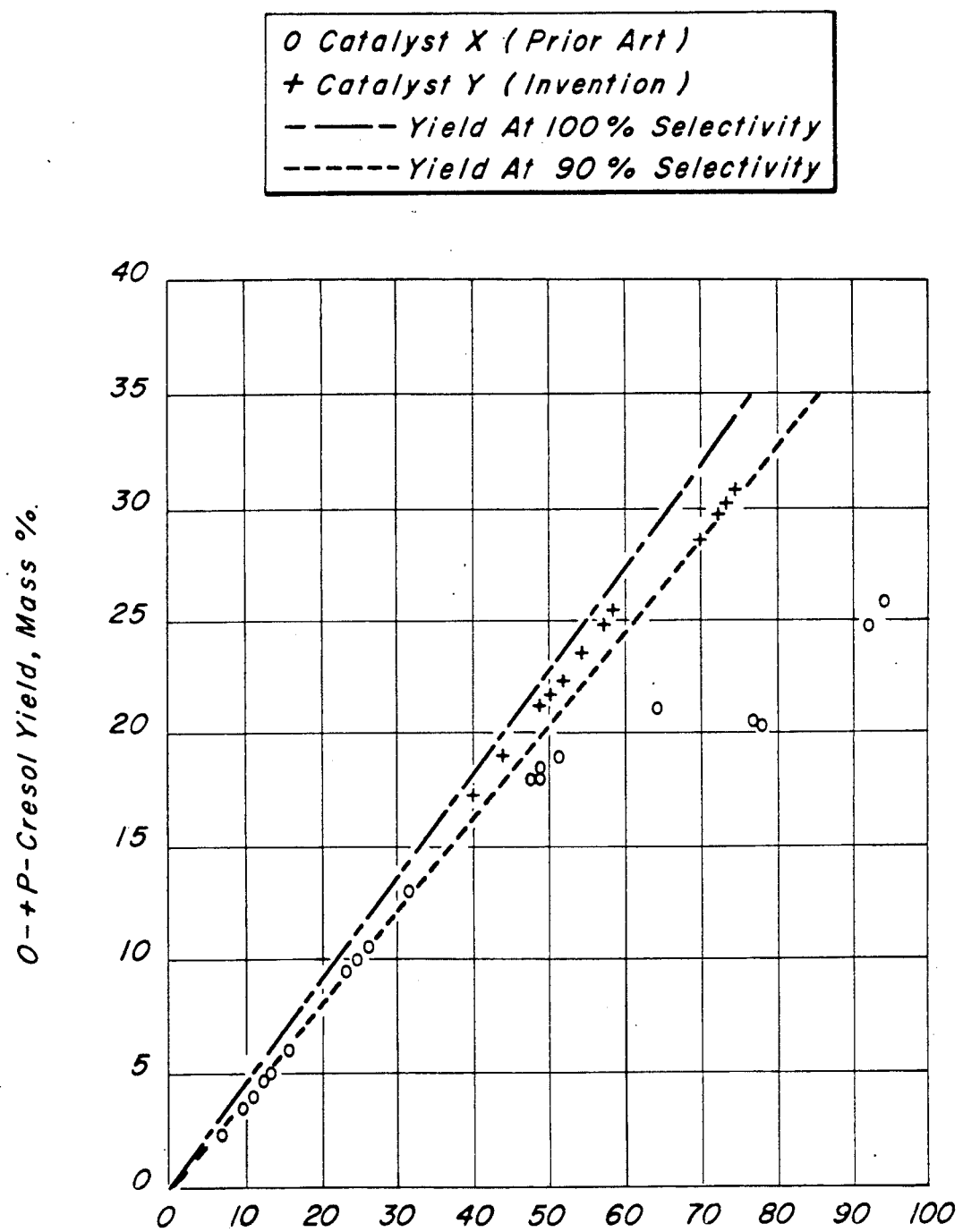
Figure

PROCESS THE ISOMERIZATION OF CRESOLS

CROSS REFERENCE TO RELATED APPLICATIONS

This application is a continuation-in-part of prior copending application Ser. No. 394,038, filed Aug. 14, 1989, now U.S. Pat. No. 4,939,110 which is a division of application Ser. No. 259,086, filed Oct. 17, 1988, now U.S. Pat. No. 4,899,012. The disclosures of these applications are incorporated herein by reference thereto.

BACKGROUND OF THE INVENTION

1. Field of the Invention

This invention relates to an improved process for the conversion of alkylphenols, particularly for the isomerization of cresols.

2. General Background

The individual cresol isomers have a wide variety of uses. Paracresol, or p-cresol, is particularly useful in disinfectants or fumigating compositions and in the synthesis of such compounds as cresotimic acid and dyestuffs. Ortho-cresol, or o-cresol, finds application as a disinfectant or in the preparation of coumarine and other organic intermediates. Meta-cresol, or m-cresol, is used in photographic and ore-flotation chemicals, paint and varnish removers, disinfectant and fumigating compositions and in the production of synthetic resins and explosives.

The relative proportions of cresol isomers in a natural or synthetic mixture of cresols would not be expected to match the proportions of each cresol isomer needed to meet product requirements. This divergence between the supply and demand proportions of cresol isomers is the driving force favoring development of a cresol isomerization process to convert surplus isomers to needed isomers.

Prior Art

Bound zeloite catalysts are widely used for conversion reactions, based on their high activity and/or selectivity. Zeolites, or crystalline aluminosilicates, may be represented by the empirical formula:

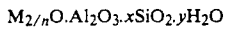

$$M_{2/n}O \cdot Al_2O_3 \cdot xSiO_2 \cdot yH_2O$$

in which n is the valence of M and x is generally equal to or greater than 2. Zeolites have skeletal structures which are made up of three-dimensional networks of $SiO_4$ and $AlO_4$ tetrahedra, corner linked to each other by shared oxygen atoms. Zeolites particularly suited for use as isomerization catalysts include mordenite and the ZSM variety.

Isomerization of o-creosol using a zeolite of the ZSM-type is disclosed in U.S. Pat. No. 4,283,571 (Keim et al.). U.S. Pat. No. 4,503,269 (Engel et al.) teaches isomerization of a cresol using a zeolite catalyst in the presence of hydrogen. Neither of these references discloses the incorporation any metals into the zeolite, however, or the use of a binder in the catalyst.

U.S. Pat. No. 3,554,900 (Bowes) teaches a method of treating a zeolite containing a catalytically active metal on its surface with a poisoning metal without affecting the catalytic activity of the interior of the zeolite. The catalytically active metal may be platinum and the poisoning metal may be lead. The compositing of the metals with the zeolite and the subsequent contacting of the support by the poisoning metal is in contradistinction to the present invention, however, and Bowes does not teach a binder. Further, Bowes discloses a hydrocracking process in a preferred embodiment which contrasts with the preferred use of the present invention.

U.S. Pat. No. 3,751,502 (Hayes et al.) discloses an isomerization process employing a catalyst comprising a platinum-group metal, a Group IV-A metallic component, and a halogen component on a carrier containing alumina and a crystalline aluminosilicate. The preferred aluminosilicate is mordenite, however, and faujasite is also taught; there is no indication that a pentasil zeolite was contemplated. Further, Hayes et al. teaches a preferred lead to platinum ratio of 0.05 to 0.09 in contradistinction to the present invention.

U.S. Pat. Nos. 3,827,971 and 3,827,988 (Kominami et al.) teach a process for producing aromatic hydrocarbons and a catalyst composition, respectively, comprising platinum, lead, another metal from a list of 25, and chlorine on a carrier such as silica-alumina, alumina hydrate, silica, zeolite, kaolin, acid clay or bentonite. Selecting a catalyst suitable for the present process from the myriad possibilities of Kominami et al. would be analogous to locating a needle in a haystack. Kominami et al. '971 and '988 both teach a catalyst that supresses isomerization, supporting the above distinctions in composition relative to the present catalyst.

U.S. Pat. No. 3,839,195 (Wilhelm) discloses a catalyst reforming process employing a catalyst comprising a platinum-group metal, lead, and a halogen component on a porous carrier, preferably alumina. A zeolite crystalline aluminosilicate is taught in the general disclosure. Wilhelm restricts the atomic ratio of lead to platinum to 0.05 to 0.9:1, however, in contradistinction to the higher ratios preferred in the more specifically defined zeolitic composite of the present process.

U.S. Pat. No. 3,887,495 (Juguin et al.) discloses a catalyst, applied in the dehydrogenation of paraffins, consisting essentially of alumina and two or more metals. Metals disclosed are rhenium plus at least one of lead, gallium, indium, thallium, germanium, tin, antimony and bismuth, or at least one each of Group VIII, plus molybdenum and tungsten, plus gallium, indium, thallium, germanium, antimony and bismuth. Juguin et al. does not teach a Group VIII metal plus lead on the same catalyst, however, and is silent with respect to the incorporation of a zeolite on the catalyst composite. Further, Juguin et al. teaches a substantially neutral catalyst in contradistinction to the present invention.

U.S. Pat. No. 3,894,104 (Chang et al.) discloses a process for aromatization of feedstocks containing heteroatoms using a zeolite catalyst containing at least one metal of Groups IB, IIA, IIB, IIIA, IVA, and VIII. These groups would include lead along with the Group VIII metals, but only magnesium, calcium, copper, zinc, cadmium, aluminum, indium, tin, ruthenium, cobalt, nickel, palladium, and platinum were specifically exemplified in the general disclosure. Zeolite in matrix form is taught, but the zeolite content is restricted to 25 to 75 percent in contradistinction to the 1 to 20 percent preferred in the present process.

U.S. Pat. No. 4,116,870 (Weisang et al.) discloses a catalyst for the treatment of hydrocarbons comprising a refractory inorganic oxide support, platinum, zirconium or titanium, tin, and a halogen component. The general disclosure teaches a porous alumina or aluminosilicate carrier and possible association of the metals lead, indium, tin, rhenium and germanium with platinum. However, this reference does not suggest the specific zeolite component of the present catalytic composite.

U.S. Pat. No. 4,152,363 (Tabak et al.) discloses a process for the isomerization of alkylaromatics employing a catalyst containing about 0.1 to 5% zeolite in a binder diluent and a Group VIII metal. However, Tabak is silent with respect to a modifier metal.

U.S. Pat. Nos. 4,331,822 and 4,485,185 (Onodera et al.) disclose a xylenes isomerization process and catalyst composition composition, respectively. The catalyst comprises a zeolite of the ZSM type and two or more metals, platinum and at least one metal selected from titanium, barium and lanthanum. A preferred embodiment comprises 1 to 99% in organic oxide binder and the general specification discloses also lead, chromium, zinc, gallium, germanium, strontium, yttrium, zirconium, molybdenum, palladium, tin, cesium, tungsten, osmium, cadmium, mercury, iridium and beryllium as the second metal. The broad disclosure of Onodera et al. does not anticipate the specific catalyst composite of the present process. Further, Onodera et al. teaches compositing of the metal components with the zeolite in contradistinction to the present invention.

When the prior art is compared with the subject matter of the present invention, it is believed that the present process for isomerizing alkylphenols is neither taught nor suggested. The unique combination of Group VII metal, lead, and relatively low pentasil zeolite content on an inorganic binder exhibits surprising results in isomerizing cresols with high selectivity.

DESCRIPTION OF THE INVENTION

Objects

It is an object of the present invention to provide a novel process for the isomerization of alkylphenols. A corollary objective of the invention is to provide an isomerization process which isomerizes cresols at high yield efficiency.

Summary of the Invention

This invention is based on the discovery that a bound zeolite catalyst containing a Group VII metal and a modifier demonstrates unexpectedly high yield efficiency when isomerizing a mixture of cresols to increase the yield of desired isomers.

Embodiments

A broad embodiment of the present invention is an alkylphenol isomerization process using a catalyst comprising a Group VII metal component and a modifier on a carrier material comprising a pentasil zeolite and an inorganic-oxide binder.

In a preferred embodiment, the feedstock of the isomerization process comprises a non-equilibrium mixture of cresol isomers.

In a highly preferred embodiment, the modifier comprises a lead component.

In an even more highly preferred embodiment, the inorganic oxide binder comprises alumina.

In an alternative embodiment, a cresol isomerization process utilizes a catalyst comprising a platinum component and a lead component wherein the atomic ratio of lead to platinum of from about 2 to about 10, from about 1 to about 20 mass % of a ZSM-5 zeolite, and an alumina binder.

These as well as other embodiments will become apparent upon a reading of the following detailed description of the invention.

BRIEF DESCRIPTION OF THE DRAWING

The accompanying drawing shows the surprising benefit of the subject invention. The "FIGURE" shows the yield efficiency of desired cresol isomers in relation to conversion or extent of isomerization.

DETAILED DESCRIPTION OF THE INVENTION

To reiterate briefly, one embodiment of the present invention is an alkylphenol isomerization process using a catalyst comprising a metal component from Group VII of the Periodic Table (see Cotton and Wilkenson, *Advanced Inorganic Chemistry*, (3rd ed., 1972) and a modifier on a carrier material comprising a pentasil zeolite and an inorganic-oxide binder.

The process of this invention finds utility in the isomerization of isomerizable alkylphenols. Alkylphenols are phenols with one or more hydrocarbon sidechains attached to the aromatic ring. The hydrocarbon sidechains may be $CH_3$, $C_2H_5$, $C_3H_7$, or $C_4H_9$ or have five or more carbon atoms. The alkylphenols thus may be, for example, cresols, xylenols, phlorol and other ethylphenols, pseudocumenol, mesitol, methylethylphenols, propylphenols, and higher alkylphenols. The feed stock to the present process may contain more than one species of alkylphenol and may contain other constituents which do not substantially interfere with the isomerization reaction. Cresols comprise the preferred feedstock to the present process.

The isomerizable alkylphenols, preferably comprising cresols, may be utilized as found in selective fractions from various refinery petroleum streams or streams derived from coal or wood processing or from upgrading of synthesis gas. For example, the feedstock to the present process may be recovered from cracking of heavy petroleum fractions, pyrolysis of petroleum distillates, caustic extraction of petroleum fractions, extraction of coal tar, or separation of Fischer-Tropsch products. The feedstock also may be derived by alkylation of phenol, e.g., with an olefin or alcohol. The preferred cresol-containing feedstock comprises one or more of the isomers p-cresol, o-cresol and m-cresol.

According to the process of the present invention, an alkylphenol charge stock, preferably in admixture with hydrogen, is contacted with a catalyst of the type described hereinafter at isomerization conditions. Contacting may be effected using the catalyst in a fixed-bed system, a moving-bed system, a fluidized-bed system, or in a batch-type operation. A batch-type operation is described in U.S. Pat. No. 4,503,269, incorporated herein by reference thereto. In view of the danger of attrition loss of the valuable catalyst and of operational advantages, it is preferred to use a fixed-bed system. In this system, a hydrogen-rich gas and the feedstock are preheated by suitable heating means to the desired reaction temperature and then passed into an isomerization zone containing a fixed bed of the hereinafter-characterized catalyst. The conversion zone may be one or more separate reactors with suitable means therebetween to ensure that the desired isomerization temperature is maintained at the entrance to each zone. It is to be noted that the reactants may be contacted with the catalyst bed in either upward, downward, or radial-flow fashion, and that the reactants may be in the liquid phase, a mixed liquid-vapor phase, or a vapor phase when contacted with the catalyst.

The process of this invention for isomerizing an isomerizable alkylphenol preferably is effected by contacting the alkylphenol-containing feedstock at isomerization conditions with a fixed bed of the hereinafter-described catalyst by passing the hydrocarbon in a down-flow fashion through the bed. Isomerization conditions include a temperature in the range of from about 0° to 600° C. and a pressure of from atmospheric to about 100 atmospheres. The temperature range preferably is about 250° to 500° C., especially 300°–450° C., and a pressure range of 2–75 atmospheres is employed. The hydrocarbon is passed into the reaction zone preferably in admixture with hydrogen at a hydrogen to alkylphenol mole ratio of about 0.5:1 to about 15:1 or more. Other inert diluents such as nitrogen, argon, methane, ethane, and the like may be present. The liquid hourly hydrocarbon space velocity of the feedstock relative to the volume of catalyst is from about 0.5 to about 30 $hr^{-1}$, and most preferably at 1 to 20 $hr^{-1}$.

The particular product recovery scheme employed is not deemed to be critical to the instant invention. Any recovery scheme known in the art may be used. Typically, the reactor effluent will be condensed with the hydrogen and other light components removed therefrom by flash separation. The condensed liquid product is then subjected to a fractionation procedure to further purify the desired liquid isomerized product. Isomerized product derived from the processing of the preferred cresol-containing feedstock preferably is further fractionated to separate one or more substantially pure cresol isomers, i.e., p-cresol, o-cresol or m-cresol. Alternatively, the cresol isomers may be separated by crystallization methods or most preferably by selective adsorption using crystalline aluminosilicates. Adsorptive processes for separating cresols are described, for example, in U.S. Pat. Nos. 3,014,078; 3,969,422 and 4,356,331, incorporated herein by reference thereto. The substantially pure cresol isomers are suitable for formulations and chemical syntheses such as those mentioned hereinabove. The raffinate remaining after recovery of the desired cresol isomers may be returned to the isomerization reactor section.

As mentioned, the catalyst of the present invention contains a pentasil zeolite. "Pentasil" is a term used to describe a class of shape-selective zeolites. This novel class of zeolites is well known to the art and is typically characterized by a silica/alumina mole ratio of at least about 12. Descriptions of the pentasils may be found in U.S. Pat. Nos. 4,159,282; 4,163,018; and 4,278,565, all of which are incorporated herein by reference. Of the pentasil zeolites, the preferred ones are ZSM-5, ZSM-8, ZSM-11, ZSM-12, ZSM-23, and ZSM-35, with ZSM-5 being particularly preferred. It is a preferred embodiment of the present invention that the pentasil be in the hydrogen form. Conversion of an alkali metal form pentasil to the hydrogen form may be performed by treatment with an aqueous solution of a mineral acid. Alternatively, hydrogen ions can be incorporated into the pentasil by ion exchange with ammonium cations, followed by calcination.

The relative proportion of pentasil zeolite in the catalyst composite is an optional feature of the present invention. The pentasil zeolite content preferably ranges from about 1 to 20 mass %, with 5 to 15 mass % preferred. There is a tradeoff between the zeolite content of the catalyst composite and the pressure and temperature of an isomerization operation in maintaining low cresol losses. Higher pressure requires higher temperature and lower zeolite content in order to avoid saturation and subsequent hydrocracking of aromatic compounds. The balance of the three parameters may result in a different optimum zeolite content for an isomerization unit designed after the present invention than for an existing unit with fixed pressure and temperature limitations.

It is also within the scope of the present invention that the particular pentasil selected may be gallosilicate. Gallosilicates have essentially the same structure as the ZSM-type zeolites described hereinabove, except that all or part of the aluminum atoms in the aluminosilicate crystal framework are replaced by gallium atoms. This substitution of the aluminum by gallium is usually performed prior to or during synthesis of the zeolite. The gallium content for this particular type of pentasil, expressed as mole ratios of $SiO_2$ to $Ga_2O_3$, ranges from 20:1 to 400:1 or more.

Considering next the inorganic oxide binder utilized in the present invention, it is preferred that the binder be a porous, adsorptive, high-surface area support having a surface of about 25 to about 500 $m^2/g$. The binder should also be uniform in composition and relatively refractory to the conditions utilized in the conversion process. By the term "uniform in composition", it is meant that the support be unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention binder materials which have traditionally been utilized in dual-functional hydrocarbon conversion catalysts such as: (1) activated carbon, coke, or charcoal; (2) silica or silica gel, silicon carbide, clays and silicates including those synthetically prepared and naturally occurring, which may or may not be acid treated, for example, attapulgus clay, diatomaceous earth, fuller's earth, kaolin, kieselguhr, etc.; (3) ceramics, porcelain, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, zirconia-alumina, etc.; and (5) combinations of one or more elements from one or more of these groups. The preferred binders for use in the present invention are refractory inorganic oxides, with best results obtained with a binder comprised of alumina. Suitable aluminas are the crystalline aluminas known as the gamma-, eta-, and theta-aluminas, with gamma-alumina as the preferred form. In addition, in some embodiments, the alumina binder may contain minor proportions of other well known refractory inorganic oxides such as silica, zirconia, magnesia, etc.; however, the preferred binder is substantially pure gamma-alumina. Preferred binders have an apparent bulk density of about 0.3 to about 0.8 g/cc and the surface area characteristics such that the average pore diameter is about 20 to 300 angstroms and the pore volume is about 0.1 to about 1 cc/g. In general, excellent results are typically obtained when the binder of the catalyst is gamma-alumina in the form of spherical or extruded particles having a relatively small diameter (i.e., typically about 1/16-inch), an apparent bulk density of about 0.4–0.7 g/cc, a pore volume of about 0.7 cc/g, and a surface of about 200–270 m$^2$/g.

The preferred alumina binder is uniform in composition and may be prepared in any suitable manner and may be synthetically prepared or naturally occurring. Whatever type of alumina is employed, it may be activated prior to use by one or more treatments including drying, calcination, steaming, etc,. and it may be in a form known as activated alumina, activated alumina of commerce, porous alumina, alumina gel, etc. For example, the alumina binder may be prepared by adding a suitable alkaline reagent, such as ammonium hydroxide to a salt of aluminum such as aluminum chloride, aluminum nitrate, etc., in an amount to form an aluminum hydroxide gel which, upon drying and calcining, is converted to alumina.

Using techniques commonly known to those skilled in the art, the catalyst of the present invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing. A preferred shape for the catalyst composite is the extrudate prepared using the well-known extrusion method. Here the pentasil zeolite is combined with the binder and a suitable peptizing agent and mixed to form a homogeneous dough or thick paste. The modifier may be added to the binder before compositing or to the mixture before shaping, either before, after, or simultaneously with the pentasil zeolite, in one embodiment as discussed later in more detail. This material is then extruded through a die pierced with multiple holes and the spaghetti-shaped extrudate is cut off on the opposite side to form short cylinders. The rheological properties of the dough mixture can be varied by the use of "extrusion aids" such as methylcellulolse, stearates, small amounts of clay, colloidal silica, etc. After extrusion, the cylinders are dried and calcined as set forth hereinbelow.

An alternative preferred shape of the subject catalytic composite is the sphere, manufactured by the well-known oil-drop method which comprises forming a hydrosol of the desired inorganic oxide binder by any of the techniques taught in the art. For example, alumina hydrosol is preferably prepared by reacting aluminum metal with hydrochloric acid. The pentasil zeolite is then uniformly dispersed in the hydrosol. This resultant zeolite-containing hydrosol is then commingled with a suitable gelling agent and is dispersed as droplets into an oil bath maintained at elevated temperatures. As discussed later, in one embodiment, the modifier may be added to the mixture prior to forming the droplets and either before, after, or simultaneously with the pentasil. The droplets of the mixture remain in the oil bath until they set and form hydrogel spheres. The spheres are continuously withdrawn from the oil bath and typically subjected to specific aging treatments in oil and an ammoniacal solution to further improve their physical charactistics. The resulting aged and gelled particles are then washed and dried at a relatively low temperature of about 100°–205° C. and subjected to a calcination procedure at a temperature of about 450°–700° C. for a period of about 1 to about 20 hours. See the teachings of U.S. Pat. No. 2,620,314 for additional details.

Another component of the present invention is the Group VII metal component. Preferably this Group VII metal is selected from the platinum-group metals, which include platinum, palladium, rhodium, ruthenium, osmium, and iridium. The preferred platinum-group metal is platinum, with palladium being the next preferred metal. The platinum-group metal component may exist within the final catalyst composite as a compound such as an oxide, sulfide, halide, oxysulfide, etc., or as an elemental metal or in combination with one or more other ingredients of the catalyst. It is believed that the best results are obtained when substantially all the platinum-group metal exists in a reduced state. The platinum-group metal generally comprises from about 0.01 to about 2 mass % of the final catalytic composite, calculated on an elemental basis. It is preferred that the platinum content of the catalyst be between about 0.05 and 1 mass %.

The platinum-group metal component may be incorporated into the catalyst composite in any suitable manner, such as by ion-exchange or impregnation of the zeolite/binder composite. The preferred method of preparing the catalyst normally involves the utilization of a water-soluble, decomposable compound of a platinum-group metal to impregnate the calcined zeolite/binder composite. For example, the platinum-group metal component may be added to the calcined hydrogel by commingling the calcined composite with an aqueous solution of chloroplatinic or chloropalladic acid.

Another essential constituent of the present invention is a modifier. The modifier may be incorporated into the catalytic composite in any suitable manner to effectively disperse this component. Suitable methods could include coprecipitation or cogelation with the inorganic oxide binder with or without the zeolite, ion-exchange with the inorganic oxide binder, or impregnation of the catalyst at any stage in the preparation. The modifier may be selected from the group consisting of lead, tin, germanium and bismuth. The preferred modifier of the catalyst is a lead component.

One effective method of incorporating the preferred lead component into the catalytic composite involves the addition of suitable soluble lead compounds such as lead nitrate, lead acetate, lead citrate, lead formate, and the like to the zeolite-containing hydrosol of the inorganic oxide, and then combining the hydrosol with a suitable gelling agent and dispersing the resulting mixture into an oil bath with subsequent processing as explained in more detail hereinabove. After calcining the gelled hydrosol, a binder material is obtained having a uniform dispersion of lead oxide in an intimate combination principally with the inorganic oxide binder. Another preferred method of incorporating the lead component into the catalyst composite involves the utilization of a soluble, decomposable compound of lead to impregnate and uniformly disperse the lead on the composite. Best results are ordinarily obtained with a solution of lead nitrate and nitric acid. In general, the lead component can be impregnated either prior to, simultaneously with, or after the platinum-group metallic component is added to the carrier material. A preferred method is to impregnate the lead component simultaneously with e platinum-group metal component. A preferred impregnation solution contains chlororplatinic acid, nitric acid, and lead nitrate.

Regardless of which lead compound is used in the preferred impregnation step, it is important that the lead component be uniformly distributed throughout the carrier material. That is, it is important that the concentration of lead in any reasonably divisible portion of the carrier material be approximately the same. In order to achieve this objective, it is necessary to maintain the pH of the impregnation solution in a range of from 7 to about 1 or less. Good platinum-lead interaction results when the nitric acid content of the impregnated carrier material is from about 1 to about 15 mass %, and a nitric acid content from about 3 to about 11 mass % is preferred.

The effective dispersion of the Group VII metal and lead components is essential to obtain the selectivity demonstrated by the catalyst of the present invention. It is believed, without limiting the present invention, that effective dispersion of the metals and avoidance of platinum crystallites results in association of the Group VIII metal and lead with resulting beneficial attenuation of the activity of the Group VIII metal. Such attenuation is believed to enhance catalyst selectivity by reducing losses to byproducts. Optimum interaction between Group VIII metal and lead components had been estimated for a large number of catalyst formulations and preparation techniques using a microreactor test of the conversion of methylcyclohexane to toluene at 450° C. and 1 atm. pressure, with 1–40% conversion, and preferable 10–30% conversion being a target value.

The amount of the lead component is optimally established as a function of the amount of Group VIII metal contained in the catalyst composite. More specifically, unanticipated beneficial interaction of the Group VIII metal component and lead component is effected at an atomic ratio of lead to Group VII metal of from about 2:1 to 10:1.

An optional constituent of the bimetallic catalyst used in the present invention is the halogen component. Although the precise form of the chemistry of the association of the halogen component with the carrier material is not entirely known, it is customary in the art to refer to the halogen component as being combined with the carrier material or with the other ingredients of the catalyst in the form of the corresponding halide (e.g. as the chloride or the fluoride). This combined halogen may be either fluorine, chlorine, iodine, bromine, or mixtures thereof. Of these, fluorine and, particularly, chlorine are preferred. The halogen may be added to the carrier material in any suitable manner either during preparation of the carrier material or before or after the addition of the other components.

For example, the halogen may be added at any stage of the preparation of the carrier material or to the calcined carrier material as an aqueous solution of a suitable decomposable halogen-containing compound such as hydrogen fluoride, hydrogen chloride, hydrogen bromide, ammonium chloride, etc. The halogen component or a portion thereof may be combined with the carrier material during the impregnation of the latter with the platinum-group component; for example, through the utilization of a mixture of chloroplatinic acid and hydrogen chloride. In another situation, the alumina by hydrosol which is one of the hereinabove preferred methods to form the alumina carrier material may contain halogen and thus contribute at least a portion of the halogen component to the final composite. In a preferred embodiment, halogen is included in the air atmosphere utilized during the final calcination step to promote dispersion of the Group VIII metal and lead components. The halogen is combined with the carrier material to result in a final composite that contains from about 0.1 to about 1.0 mass % halogen, calculated on an elemental basis.

Regardless of the details of how the components of the catalyst are combined with the porous carrier material, the catalyst composite will be dried at a temperature of from about 100° to about 320° C. for a period of from about 2 to about 24 or more hours. The dried composite is finally calcined at a temperature of from about 400° to about 600° C. in an air atmosphere for a period of from about 0.1 to about 10 hours to convert the metallic compounds substantially to the oxide form. The chloride content of the catalyst is adjusted by including a halogen or halogen-containing compound in the air atmosphere. The use of both chlorine and hydrogen chloride is particularly preferred.

The resultant calcined composite is subjected to a substantially water-free reduction step prior to its use in the conversion of hydrocarbons. This step is designed to insure a uniform and finely divided dispersion of the metallic components. Preferably, substantially pure and dry hydrogen (i.e., less than 20 vol. ppm $H_2O$) is used as the reducing agent in this step. The reducing agent contacts the catalyst at conditions, including a temperature of from about 200° to about 650° C. and for a period of from about 0.5 to about 10 hours, effective to reduce substantially all of the Group VII metal component to the metallic state.

EXAMPLES

The following examples will serve to illustrate certain specific embodiments of the present invention. These examples should not, however, be construed as limiting the scope of the invention as set forth in the claims. There are many possible other variations, as those of ordinary skill in the art will recognize, which are within the spirit of the invention.

One catalyst each of the prior art and of the present invention were prepared as described hereinafter and evaluated for isomerization of cresols. Relative performance was assessed by comparing yield efficiency at a range of isomerization conversion levels.

EXAMPLE 1

Catalyst X represents a catalyst of the prior art. This catalyst consisted essentially of approximately 11 mass % hydrogen-form ZSM-5 zeolite with the remainder being alumina binder. The zeolite was added to an alumina sol solution, prepared by digesting metallic aluminum in hydrochloric acid, in an amount sufficient to yield a zeolite content in the finished catalyst of about 11 mass %. A second solution of hexamethylenetetramine (HMT) was prepared and added to the zeolite/alumina sol mixture to give homogeneous admixture. This admixture was then dispersed as droplets into an oil bath maintained at about 93° C. The droplets remained in the oil bath at 150° C. until they set and formed hydrogel spheres. These spheres were removed from the oil bath, water washed with a 0.5% ammonia/water solution, air dried, and calcined at a temperature of about 650° C.

EXAMPLE 2

Catalyst Y was prepared in accordance with the invention, and comprised approximately 11 mass % hydrogen-form ZSM-5 zeolite, 0.23 mass % platinum and 0.51 mass % lead, with the remainder being alumina binder. The lead/platinum atomic ratio thus was about 2.0:1. The spherical catalyst was prepared by the oil-drop method in the same manner as Catalyst A, with the lead added as $Pb(NO_3)_2$ by coimpregnation along with platinum as chloroplatinic acid in a solution with 4 mass % hydrochloric acid and 3.5 mass % nitric acid based on the support. The impregnated spheres were oxidized at 525° C., chloride-adjusted to 0.6 mass % Cl at 525° C. and reduced in $H_2$ at 565° C.

EXAMPLE 3

A feedstock of pure m-cresol was dried and isomerized in a pilot-plant test to compare the performance of Catalysts X and Y. Pilot-plant operating conditions comprised a temperature range of 350°–450° C., pressure of about 60 atmospheres, and liquid hourly space velocity of 1.0 $hr^{-1}$. The temperature was varied within the indicated ranges to develop a relationship between the degree of isomerization and product selectivity for each of Catalysts X and Y, as discussed below and illustrated in the FIGURE.

Comparative selectivity for Catalysts X and Y is shown in the FIGURE. Results are plotted as mass % yield of (p-cresol+o-cresol), relative to the m-cresol feedstock, against the % of equilibrium (p-cresol+o-cresol) in total cresols in the isomerized product. The cresol equilibrium composition was taken to be 55% m-cresol, 23% p-cresol and 22% o-cresol. Yields of (p-cresol +o-cresol) corresponding to 90% and 100% selectivity are plotted as diagonal lines. The FIGURE shows that selectivity for Catalyst Y of the invention is 9% or more in all of the tests, while Catalyst X of the prior art demonstrates much lower selectivity.

We claim as our invention:

1. A process for the isomerization of a feedstock containing a non-equilibrium mixture of cresols which comprises contacting such non-equilibrium mixture at isomerization conditions with a catalyst comprising a combination of a Group VII metal component and a modifier with a carrier material containing a pentasil zeolite and an inorganic oxide binder to produce an isomerized product.

2. The process of claim 1 wherein the isomerization conditions comprise a temperature in the range of about 250° C. to about 500° C., a pressure of from about 1 to 75 atmospheres, and a liquid hourly space velocity of from about 0.5 to 30 $hr^{-1}$.

3. The process of claim 1 wherein the Group VII metal component comprises platinum in an amount of about 0.01 to 2 mass % of the catalyst.

4. The process of claim 1 wherein the modifier is selected from the group consisting of lead, tin, germanium and bismuth.

5. The process of claim 1 wherein the modifier comprises a lead component.

6. The process of claim 5 wherein the atomic ratio of lead to Group VIII metal is about 2 to 10.

7. The process of claim 1 wherein the pentasil zeolite comprises from about 1 to 20 mass % of the carrier material.

8. The process of claim 1 wherein the pentasil zeolite comprises from about 5 to 15 mass % of the carrier material.

9. The process of claim 1 wherein the pentasil zeolite is selected from the Group consisting of ZSM-5, ZSM-11, ZSM-12, ZSM-23, ZSM-35, and ZSM-38.

10. The process of claim 1 wherein the pentasil zeolite is ZSM-5.

11. The process of claim 1 wherein the inorganic oxide binder comprises gamma-alumina.

12. The process of claim 1 wherein the catalyst comprises a halogen component.

13. The process of claim 1 further comprising the recovery of one or more cresol isomers from the isomerized product.

14. A process for the isomerization of a feedstock containing a non-equilibrium mixture of cresols which comprises:
 (a) contacting the non-equilibrium mixture as isomerization conditions with a catalyst comprising a combination of a platinum component and a lead component with a carrier material containing about 1 to 20 mass % of a pentasil zeolite and an inorganic oxide binder to produce an isomerized product, and
 (b) recovery of one or more cresol isomers from the isomerized product.

15. A process for the isomerization of a feedstock containing a non-equilibrium mixture of cresols which comprises:
 (a) contacting the non-equilibrium mixture at isomerization conditions with a catalyst comprising a combination of a platinum component and a lead component with a carrier material containing about 1 to 20 mass % of a pentasil zeolite and an inorganic oxide binder, wherein the atomic ratio of lead to platinum is about 2 to 10, to produce an isomerized product, and
 (b) recovery of one or more cresol isomers from the isomerized product.

* * * * *

UNITED STATES PATENT AND TRADEMARK OFFICE
CERTIFICATE OF CORRECTION

PATENT NO. : 5,053,558
DATED      : OCTOBER 1, 1991
INVENTOR(S) : SACHTLER et al.

It is certified that error appears in the above-identified patent and that said Letters Patent is hereby corrected as shown below:

In Column 11, lines 39 and 49, change "VII" to --VIII--.

Signed and Sealed this

Ninth Day of February, 1993

Attest:

STEPHEN G. KUNIN

Attesting Officer

Acting Commissioner of Patents and Trademarks